United States Patent
Yao et al.

(10) Patent No.: US 11,648,519 B2
(45) Date of Patent: May 16, 2023

(54) SYSTEMS FOR CONVERTING LIGHT PARAFFINS TO ALCOHOLS

(71) Applicant: PHILLIPS 66 COMPANY, Houston, TX (US)

(72) Inventors: Jianhua Yao, Bartlesville, OK (US); Anthony O. Baldridge, Bartlesville, OK (US); Neal D. McDaniel, Ochelata, OK (US); James A. Suttil, Honeywood (AU); Chengtian Wu, Bartlesville, OK (US); Dhananjay B. Ghonasgi, Bartlesville, OK (US); Maziar Sardashti, Timnath, CO (US); Bruce B. Randolph, Sachse, TX (US)

( * ) Notice: Subject to any disclaimer, the term of this patent is extended or adjusted under 35 U.S.C. 154(b) by 207 days.

(21) Appl. No.: 17/153,390

(22) Filed: Jan. 20, 2021

(65) Prior Publication Data

US 2021/0220788 A1 Jul. 22, 2021

Related U.S. Application Data

(60) Provisional application No. 62/964,310, filed on Jan. 22, 2020.

(51) Int. Cl.
*B01J 8/04* (2006.01)
*C07C 29/88* (2006.01)
*C10L 1/02* (2006.01)
*B01J 31/06* (2006.01)

(52) U.S. Cl.
CPC ............. *B01J 8/0492* (2013.01); *B01J 31/06* (2013.01); *C07C 29/88* (2013.01); *C10L 1/02* (2013.01); *B01J 2231/645* (2013.01); *B01J 2531/002* (2013.01)

(58) Field of Classification Search
CPC ............ B01J 2231/645; B01J 2531/002; B01J 31/06; B01J 31/10; B01J 8/02; B01J 8/04; B01J 8/0492; B01J 8/08; B01J 8/18; C07C 29/88; C10L 1/02
See application file for complete search history.

(56) References Cited

U.S. PATENT DOCUMENTS

| 7,057,081 B2* | 6/2006 | Allison | C07C 29/06 568/910.5 |
| 2017/0044447 A1* | 2/2017 | Pigourier | C10L 1/06 |
| 2018/0186707 A1* | 7/2018 | Abudawoud | C07C 2/12 |

* cited by examiner

*Primary Examiner* — Latosha Hines
(74) *Attorney, Agent, or Firm* — Phillips 66 Company (57) ABSTRACT

Systems for the catalytic activation and/or dehydrogenation of a paraffin feed stream that is enriched in C5 alkanes to produce olefins that are then hydrated in the presence of water to produce C5 alcohols. Optionally, paraffin isomers are separated and the n-paraffins isomerized prior to catalytic activation and/or dehydrogenation.

14 Claims, 3 Drawing Sheets

SYSTEMS FOR CONVERTING LIGHT PARAFFINS TO ALCOHOLS

CROSS-REFERENCE TO RELATED APPLICATIONS

This application is a non-provisional application that claims the benefit of and priority to U.S. Provisional Application Ser. No. 62/964,310 filed Jan. 22, 2020, titled "Systems for Converting Light Paraffins to Alcohols", which is hereby incorporated by reference in its entirety.

STATEMENT REGARDING FEDERALLY SPONSORED RESEARCH OR DEVELOPMENT

None.

FIELD OF THE INVENTION

The processes and systems detailed herein relate to the catalytic activation and/or dehydrogenation of a paraffin feed stream that is enriched in C5 alkanes to produce olefins that are then hydrated in the presence of water to produce C5 alcohols.

BACKGROUND

Increased co-production of light hydrocarbons from U.S. shale formations has created an overabundance of light paraffins, with a consequent decrease in value per barrel. Increased ethanol blending into gasoline has further exacerbated the issue. Thus, improved processes and systems are needed that can convert these feed streams to useful products, including products that meet the specifications (including octane rating and Reid vapor pressure) for a transportation fuel blend stock.

BRIEF SUMMARY OF THE DISCLOSURE

Certain embodiments of the inventive processes and systems described herein comprise a system for upgrading a paraffins feed stream to produce liquid transportation fuels comprising: a) a first separator operable to receive and separate a paraffins feed stream comprising at least 50 volume percent of paraffins that contain from five to seven carbon atoms to produce a first stream that predominantly comprises paraffins containing five carbon atoms and a second stream predominantly comprising paraffins that contain six or seven carbon atoms; b) a dehydrogenation reactor containing at least one catalyst bed that contains at least one dehydrogenation catalyst, the dehydrogenation reactor operable to receive the first stream and to facilitate contact between the first stream and the dehydrogenation catalyst at a temperature and a pressure that facilitates catalytic olefination of paraffins in the first stream by the dehydrogenation catalyst to produce a dehydrogenation effluent that is characterized by an increased olefins content relative to the first stream; c) a hydration reactor containing at least one catalyst bed that contains at least one dehydrogenation catalyst, the hydration reactor operable to receive the dehydrogenation effluent and to facilitate contact between the dehydrogenation effluent and the hydration catalyst in the presence of water at a temperature and a pressure that facilitates catalytic conversion of the dehydrogenation effluent to alcohols by the hydration catalyst to produce a hydration effluent that is characterized by an increased alcohol content (in mol. %) relative to the alcohol content of the dehydrogenation effluent; d) a second separator operable to receive the hydration effluent and to separate the hydration effluent to produce an alcohol stream that predominantly comprises alcohols and a recycle stream that predominantly comprises paraffins and olefins; e) a conduit operable to convey the recycle stream to a be combined with the first stream.

In certain embodiments of the system, the dehydrogenation reactor is operable to maintain a temperature in the range from 500° C. to 650° C. and a pressure in the range from 0 psia to 75 psia. In certain embodiments of the system, the dehydrogenation catalyst comprises one or more metals on a solid support, wherein the one or more metals are selected from Au, Ce, Cr, Cs, Cu, Ga, Fe, Mg, Pt, Pd, Sn, W and Zn.

In certain embodiments of the system, the hydration reactor is operable to maintain a temperature in the range from 0° C. to 150° C. and a pressure in the range from 0 psia to 250 psia. In certain embodiments of the system, the hydration catalyst comprises a solid acid catalyst.

Certain embodiments of the system further comprise a conduit that is operable to receive and convey the second stream to a blending apparatus that is operable to blend the second stream into a liquid transportation fuel.

Certain embodiments comprise a system for upgrading a paraffins feed stream to produce liquid transportation fuels, comprising: a) a first separator operable to receive and separate a paraffins feed stream comprising at least 50 volume percent of paraffins that contain from five to seven carbon atoms to produce a first stream predominantly comprising iso-pentane, a second stream predominantly comprising n-pentane and a third stream predominantly comprising paraffins that contain six or seven carbon atoms; b) a dehydrogenation reactor containing at least one catalyst bed comprising at least one dehydrogenation catalyst, the dehydrogenation reactor operable to receive the first stream and to facilitate contact between the first stream and the dehydrogenation catalyst at a temperature and a pressure that facilitates catalytic olefination of paraffins in the first stream by the dehydrogenation catalyst to produce a dehydrogenation effluent that is characterized by an increased olefins content relative to the first stream; c) an isomerization reactor containing at least one catalyst bed comprising at least one isomerization catalyst, the isomerization reactor operable to receive the second stream and facilitate contact between the second stream, the isomerization catalyst and a hydrogen stream at a temperature and a pressure that facilitates catalytic isomerization of n-pentane by the isomerization catalyst to produce an isomerization effluent comprising an increased content (in mol. %) of isopentane relative to the second fraction; d) a conduit operable to receive, convey and combine the isomerization effluent to with the paraffins feed stream; e) a hydration reactor containing at least one catalyst bed comprising at least one hydration catalyst, the hydration reactor operable to receive the dehydrogenation effluent and to facilitate contact between the dehydrogenation effluent and the hydration catalyst in the presence of water at a temperature and a pressure that facilitates catalytic conversion of the dehydrogenation effluent to alcohols by the hydration catalyst to produce a hydration effluent that is characterized by an increased alcohol content (in mol. %) relative to the alcohol content of the dehydrogenation effluent; f) a second separator operable to receive the hydration effluent and to separate the hydration effluent to produce an alcohol stream that predominantly comprises alcohols and a recycle stream that predominantly comprises paraffins and olefins; g) a conduit operable to receive, convey and combine the recycle stream with the first stream.

In certain embodiments of the system, the dehydrogenation reactor is operable to maintain a temperature in the range from 500° C. to 650° C. and a pressure in the range from 0 psia to 75 psia.

In certain embodiments of the system, the dehydrogenation catalyst comprises one or more metals on a solid support, wherein the one or more metals are selected from Au, Ce, Cr, Cs, Cu, Ga, Fe, Mg, Pt, Pd, Sn, W and Zn.

In certain embodiments of the system, the hydration reactor is operable to maintain a temperature in the range from 0° C. to 150° C. and a pressure in the range from 0 psia to 250 psia.

In certain embodiments of the system, the hydration catalyst comprises a solid acid catalyst.

In certain embodiments of the system, the isomerization reactor comprises more than one isomerization reactor arranged in series configuration, each isomerization reactor comprising at least one catalytic bed containing at least one isomerization catalyst.

In certain embodiments of the system, the isomerization reactor is operable to maintain a temperature in the range of 14° C. to 350° C. and a pressure in the range from 200 to 600 psig.

Certain embodiments further comprise a conduit that is operable to receive and convey the third stream to a blending apparatus that is operable to blend the third fraction with at least one hydrocarbon stream to produce a blended fuel that meets all applicable regulatory requirements for a liquid transportation fuel.

BRIEF DESCRIPTION OF THE DRAWINGS

A more complete understanding of the present invention and the benefits thereof may be acquired by referring to the following description taken in conjunction with the accompanying drawings in which.

Specific embodiments are shown by way of example in the drawings, but the inventive processes and systems may include various modifications that are not depicted in the drawings. The drawings are not intended to limit the scope of the invention to the particular embodiments illustrated and may not be to scale.

DETAILED DESCRIPTION

The process generally comprises the catalytic olefination of a paraffins feed stream that contains pentanes to produce olefins that are then hydrated in the presence of water to produce C5 alcohols that possess the characteristics that meet specifications for a gasoline blend stock. Certain embodiments additionally comprise an initial separation of the paraffins feed stream to divert C6+ paraffins, which are utilized directly as gasoline blend stock without being catalytically converted by the process. Certain embodiments are further operable to separate i-pentane from n-pentane, converting only the i-pentane to olefins, while diverting the n-pentane together with C6+ hydrocarbons to be utilized as gasoline blend stock. Finally, certain embodiments are operable to perform a 3-way separation of the paraffins feed stream to isolate i-pentane, n-pentane and C6+ paraffins. The i-pentane is first converted to olefins, then hydrated to alcohols, the n-pentane is isomerized to i-pentane that is then converted to olefins and hydrated to alcohols and the C6+ paraffins are utilized as gasoline blend stock without being catalytically converted by the process.

In general, converting pentanes to C5 alcohols produces products that are characterized by an increased octane rating and a decreased Reid vapor pressure. In one non-limiting example, isopentane is characterized by a Reid vapor pressure (RVP) of 20.5 psia and an octane rating ((RON+MON)/2) of 91. Olefination of isopentane typically produces 2-methyl 2-butene, which has a decreased RVP of 14.3 psia (relative to isopentane) but an identical octane rating of 91. According to the present inventive process, subsequent hydration of 2-methyl 2-butene to produce 2-methyl-2-butanol (or tert-amyl alcohol) gives a final product characterized by an RVP of 7.0 psia and an octane rating of 97. Thus, this 2-methyl-2-butanol product has greatly improved properties as a gasoline blend stock relative to the isopentane feed.

Figure 1:
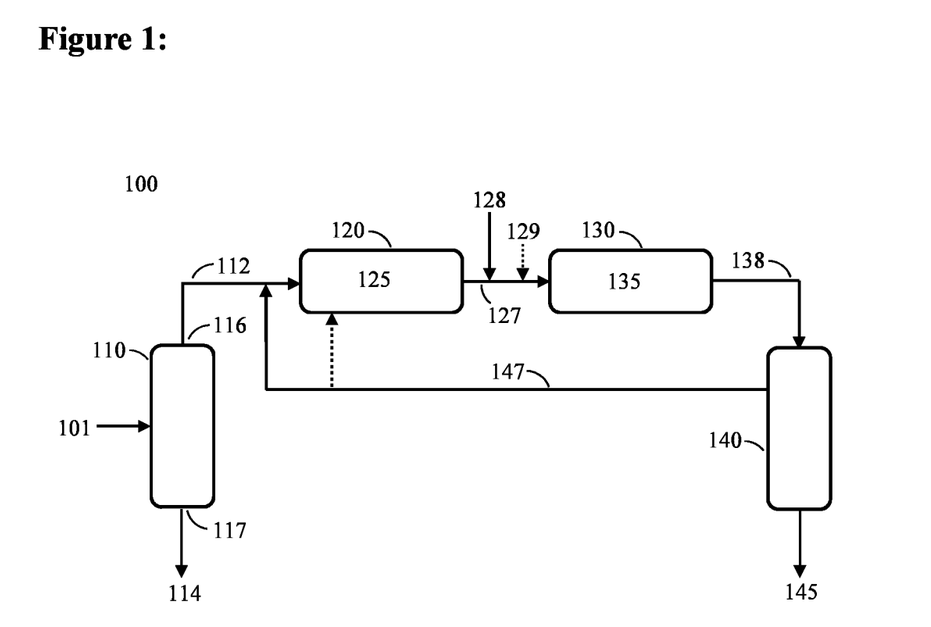
FIG. 1 is a simplified process flow diagram in accordance with a first embodiment of the inventive process and system.

A first embodiment is described in conjunction with the process and system flow diagram depicted in FIG. 1. In a system 100, A paraffins feed stream 101 that is enriched in C5 paraffins and comprises hydrocarbons containing from four to nine carbon atoms is received and separated by a first separator 110. Speaking generally, the first separator may comprise a de-pentanizer, a C5 splitter, a three-phase separator or any other separator that is operable to separate C5 paraffins and lighter hydrocarbons from hydrocarbons comprising six or more carbon atoms (C6+) and/or operable to separate iso-pentane (i-C5) from n-pentane (n-C5). The technology behind such separators is conventional and well-understood by those having skill in the art. Thus, they will not be described here in greater detail.

Referring again to the embodiment depicted in FIG. 1, first separator 110 separates the paraffins feed stream 101 to produce a first stream 112 that predominantly comprises C5 paraffins and a second stream 113 that predominantly comprises C6 paraffins, but may additionally comprise some residual C7+ hydrocarbons. The first stream 112 exits the first separator 110 via a first separator first outlet 117, and second stream 113 exits the first separator 110 via a first separator second outlet 118. The first stream 112 is conveyed via a conduit to be received by a dehydrogenation reactor 120 that comprises at least one catalytic bed containing at least one dehydrogenation catalyst 125. The second stream 113 is conveyed via conduit to be received by a blending apparatus 114 that additionally receives at least one hydrocarbon stream 115 that generally comprises hydrocarbons that are suitable for blending into liquid transportation fuels. The blending apparatus 114 mixes the second stream 113 with the at least one hydrocarbon stream 115 to produce a blended fuel 116 that meets all applicable regulatory requirements for a liquid transportation fuel, including but not limited to gasoline, jet fuel and diesel.

Speaking generally, the dehydrogenation catalyst may comprise a combination of distinct dehydrogenation catalysts, or alternatively may comprise separate beds that each comprise one or more distinct dehydrogenation catalysts.

Referring again to the embodiment depicted in FIG. 1, the dehydrogenation reactor 120 is operable to facilitate contact between the first stream 112 and the dehydrogenation catalyst 125 at a temperature and a pressure that facilitates catalytic conversion of paraffins in the first stream 112 to produce olefins, thereby producing a dehydrogenation effluent 127 that comprises an increased wt. % of olefins relative to the first stream 112. The dehydrogenation effluent 127 exits the dehydrogenation reactor 120 and is combined with a water stream 128, then conveyed via conduit to a hydration reactor 130 that contains at least one catalytic bed containing at least one hydration catalyst 135. The hydration reactor 130 is operable to facilitate contact between the dehydrogenation effluent 127 and the hydration catalyst 135 at a temperature and a pressure that facilitates catalytic conversion of olefins in the dehydrogenation effluent 127 to alcohols, thereby producing a hydration effluent 138 that leaves the hydration reactor 130 via a conduit and is conveyed to an alcohol separator 140. The alcohol separator 140 is operable to separate alcohols from paraffins and olefins to provide an alcohol stream 145 that is enriched in C5+ alcohols relative to the hydration effluent 138 and a recycle stream 147 that comprises paraffins and olefins that were present in the hydration effluent 138 but were not converted to alcohols in the hydration reactor 130.

Speaking generally, the alcohol separator may utilize any of a number of conventional technologies to effectively separate alcohols from paraffins and olefins present in the hydration effluent. Such technologies may include, but are not limited to, extractive distillation, azeotropic distillation, pervaporation membrane separation (e.g., graphene oxide membrane separation) to remove water followed by azeotropic distillation, pressure swing azeotropic distillation, adsorption. Such methods are understood by those having experience in the relevant art, and thus will not be described in greater detail here.

Referring again to the embodiment depicted in FIG. 1, the recycle stream 147 is conveyed back to be combined with the first stream 112 at a point that is downstream from the first separator 110 and upstream from dehydrogenation reactor 120. Optionally, the recycle stream 147 may be returned directly to the dehydrogenation reactor 120 (dotted line).

Figure 2:
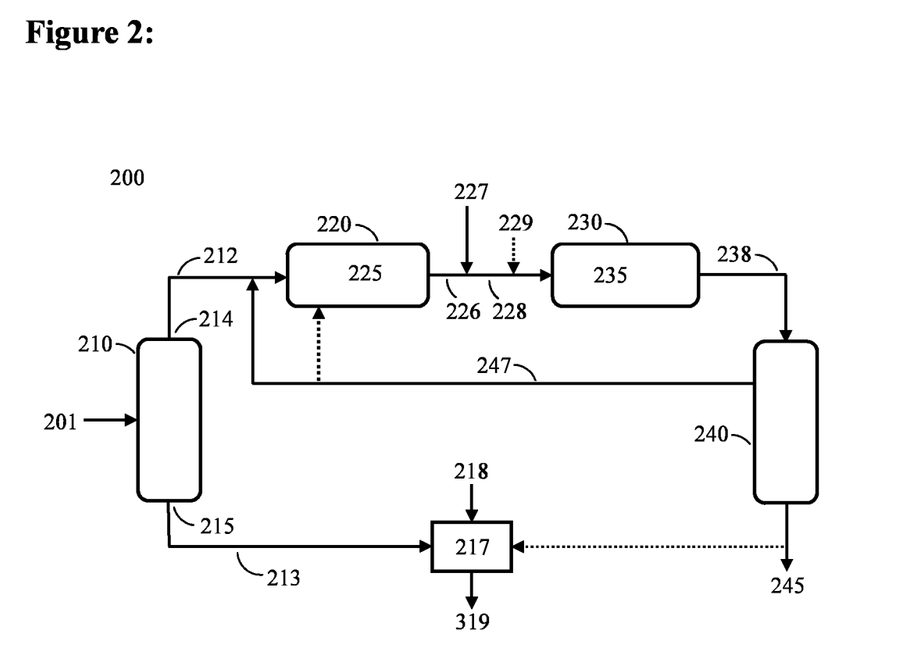
FIG. 2 is a simplified process flow diagram in accordance with a second embodiment of the inventive process and system.

A second embodiment is described in conjunction with the process and system flow diagram depicted in FIG. 2. In a system 200, a paraffins feed stream 201 that is enriched in C5 paraffins is received by a first separator 210 that is a C5 splitter operable to separate i-pentane and lighter hydrocarbons from n-pentane and C6+ hydrocarbons. The first separator 210 thus separates the paraffins feed stream 201 to produce a first stream 212 that predominantly comprises iso-pentane and a second stream 213 that predominantly comprises n-pentane but may additionally comprise some C6+ hydrocarbons. The second stream 213 may be further upgraded to a liquid transportation fuel blend stock in one of many refinery processes or utilized directly as a gasoline blend stock. The first stream 212 exits the first separator 210 via a first separator first outlet 214, and the second stream 213 exits the first separator 210 via a second separator second outlet 215. The first stream 212 is conveyed via conduit to be received by a dehydrogenation reactor 220 that comprises at least one catalytic bed that contains at least one dehydrogenation catalyst 225. The second stream 213 is conveyed via conduit to be received by a blending apparatus 217 that additionally receives at least one hydrocarbon stream 218 that generally comprises hydrocarbons that are suitable for blending into liquid transportation fuels. The blending apparatus mixes the second stream 213 with the at least one hydrocarbon stream 218 to produce a blended fuel 219 that meets all applicable regulatory requirements for a liquid transportation fuel, including but not limited to gasoline, jet fuel and diesel.

The dehydrogenation reactor 220 is operable to facilitate contact between the i-pentane stream 212 and the dehydrogenation catalyst 225 at a temperature and a pressure that facilitates catalytic conversion of paraffins in the first stream 212 to produce olefins, thereby producing a dehydrogenation effluent 226 that comprises an increased wt. % of olefins (predominantly 2-methyl-2-butene) relative to the first stream 212. The dehydrogenation effluent 226 exits the dehydrogenation reactor 220, is combined with a water stream 227 to produce a mixed dehydrogenation effluent 228 that is conveyed to a hydration reactor 230 that contains at least one bed of a hydration catalyst 235. An isopropanol stream 229 may optionally be combined with the mixed dehydrogenation effluent 228 to improve miscibility between water stream 227 and olefins in the dehydrogenation effluent 226.

The hydration reactor 230 is operable to facilitate contact between the mixed dehydrogenation effluent 228 and the hydration catalyst 235 at a temperature and a pressure that facilitates catalytic conversion of olefins in the mixed dehydrogenation effluent 228 to alcohols, thereby producing a hydration effluent 238 predominantly comprising 2-methyl-2-butanol (i.e., iso-amyl alcohol) that exits the hydration reactor 230 and is conveyed via a conduit to an alcohol separator 240. The alcohol separator 240 is operable to separate alcohols from both paraffins and olefins to produce an alcohol stream 245 that is enriched in C5+ alcohols (predominantly 2-methy-2-butanol) relative to the hydration effluent 238 and a recycle stream 247 that predominantly comprises i-pentane and 2-methyl-2-butene that were present in in the dehydrogenation effluent 226 but that were not converted to alcohols in the hydration reactor 230.

The recycle stream 247 is combined with the first stream 212, typically at a point that is downstream from the first separator 210 and upstream from dehydrogenation reactor 220. Optionally, the recycle stream 247 is returned directly to the dehydrogenation reactor 220 (dotted line). Optionally, at last a portion of the alcohol stream 245 may be conveyed (dotted line) to blending apparatus 217 to be combined with the third stream 213 and the at least one hydrocarbon stream 218 to produce blended fuel 219.

Figure 3:
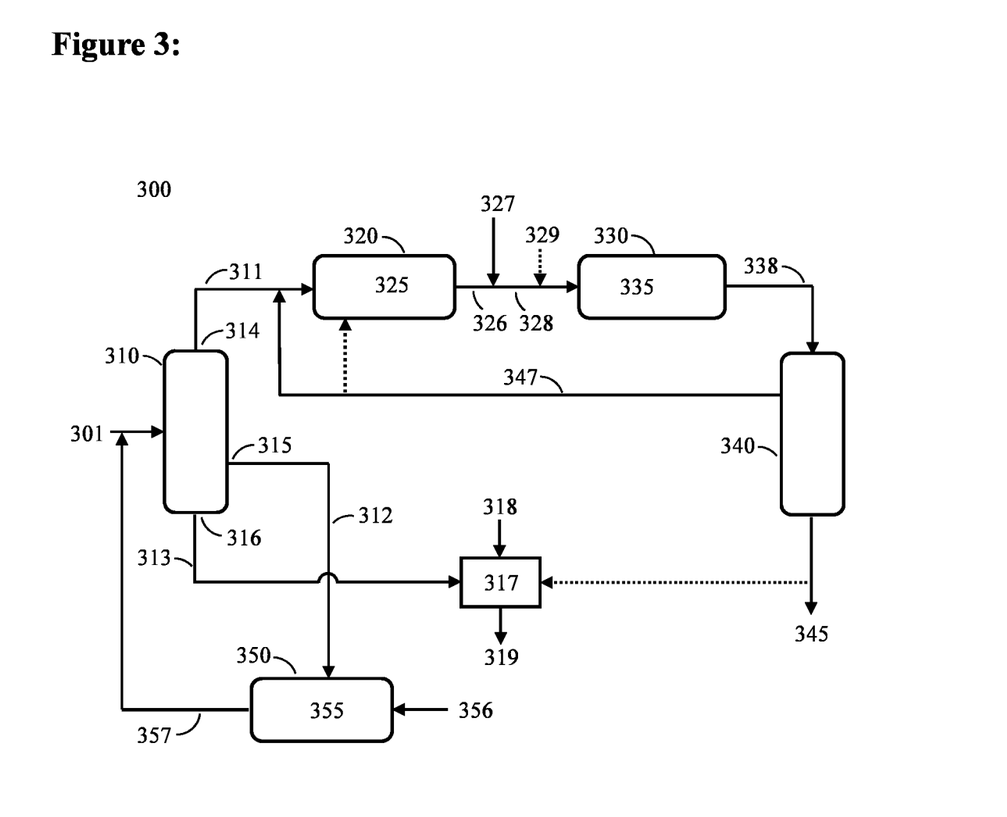
FIG. 3 is a simplified process flow diagram in accordance with a third embodiment of the inventive process and system.

A third embodiment is described in conjunction with the process and system flow diagram depicted in FIG. 3. In a system 300, a paraffins feed stream 301 that is enriched in C5 paraffins is received by a first separator 310 that is a three-phase splitter operable to separate the paraffins feed stream 301 into a first stream 311 that predominantly comprises iso-pentane, a second stream 312 that predominantly comprises n-pentane and a third stream 313 that predominantly comprises C6-C7 hydrocarbons, but that may additionally comprise a small percentage of C8-C9 hydrocarbons. The third stream 313 may be further upgraded to a liquid transportation fuel blend stock in one of many refinery processes or utilized as a gasoline blend stock without further conversion or upgrading. The third stream 313 is conveyed via conduit to be received by a blending apparatus 317 that additionally receives at least one hydrocarbon stream 318 that generally comprises hydrocarbons that meet specifications for blending into liquid transportation fuels. The blending apparatus 317 mixes the third stream 313 with the at least one hydrocarbon stream 318 to produce a blended fuel 319 that meets all applicable regulatory requirements for a liquid transportation fuel, including but not limited to gasoline, jet fuel and diesel.

The first stream 311 exits the first separator 310 via a first separator first outlet 314, the second stream 312 exits the first separator via first separator second outlet 315 and third stream 313 exits the first separator 310 via a first separator third outlet 316. The first stream 311 is conveyed via conduit to be received by a dehydrogenation reactor 320 that comprises at least one bed of a dehydrogenation catalyst 325. The dehydrogenation reactor 320 is operable to facilitate contact between the first stream 311 and the dehydrogenation catalyst 325 at a temperature and a pressure that facilitates catalytic conversion of paraffins in the first stream 311 to produce olefins, thereby producing a dehydrogenation effluent 326 that comprises an increased wt. % of olefins (predominantly 2-methyl-2-butene) relative to the first stream 311. The dehydrogenation effluent 326 exits the dehydrogenation reactor 320, is combined with a water stream 327 to produce a mixed dehydrogenation effluent 328 that is conveyed to a hydration reactor 330 that contains at least one bed of a hydration catalyst 335. An isopropanol stream 329 may optionally be combined with the mixed dehydrogenation effluent 328 to improve miscibility between water stream 327 and olefins in the dehydrogenation effluent 326.

The hydration reactor 330 is operable to facilitate contact between the mixed dehydrogenation effluent 328 and the hydration catalyst 335 at a temperature and a pressure that facilitates catalytic conversion of olefins in the mixed dehydrogenation effluent 328 to alcohols, thereby producing a hydration effluent 338 predominantly comprising 2-methyl-2-butanol (i.e., iso-amyl alcohol) that exits the hydration reactor 330 and is conveyed via a conduit to an alcohol separator 340. The alcohol separator 340 is operable to separate alcohols from both paraffins and olefins to produce an alcohol stream 345 that is enriched in C5+ alcohols (predominantly 2-methy-2-butanol) relative to the hydration effluent 338 and a recycle stream 347 that predominantly comprises i-pentane and 2-methyl-2-butene that were present in in the dehydrogenation effluent 326 but that were not converted to alcohols in the hydration reactor 330. The alcohol stream 345 is characterized by an increased octane rating and a decreased Reid vapor pressure relative to the paraffins feed stream 301 and may be utilized as a gasoline blend stock without further conversion or upgrading. Optionally, at last a portion of the alcohol stream 345 may be conveyed (dotted line) to blending apparatus 317 to be combined with the third stream 313 and the at least one hydrocarbon stream 318 to produce blended fuel 319.

The recycle stream 347 is combined with the first stream 312 at a point that is downstream from the first separator 310 and upstream from dehydrogenation reactor 320. Optionally, the recycle stream 347 is returned directly to the dehydrogenation reactor 320 (dotted line).

As mentioned earlier, the second stream 312 exits the first separator 310 via the first separator second outlet 318 and is conveyed to an isomerization reactor 350 containing at least one catalytic bed that contains at least one isomerization catalyst 355. The isomerization reactor 350 further comprises an inlet that receives a hydrogen stream 356.

Speaking generally, the isomerization reactor may optionally contain more than one isomerization catalyst. Optionally, the isomerization reactor may comprise multiple isomerization reactors arranged in series configuration (not depicted), with each isomerization reactor containing at least one isomerization catalyst.

Referring again to the embodiment depicted in FIG. 3, the isomerization reactor 350 is maintained at a temperature and pressure that facilitates the catalytic isomerization of at least a portion of the n-pentane in the second stream 312 to i-pentane, thereby producing an isomerization effluent 357 that is characterized by an increased ratio of i-pentane to n-pentane (relative to the corresponding ratio of the second stream 312). The isomerization effluent 357 is mixed with the paraffins feed stream 301, typically at a location that is upstream from the first separator 310.

Speaking generally, the effect of combining the isomerization effluent with the paraffins feed stream at a point that is upstream from the first separator is to allow the first separator to separate out i-pentane that is produced in the isomerization reactor and combine it with i-pentane from the paraffins feed stream to form the first stream that is conveyed to the dehydrogenation reactor.

Speaking generally, the isomerization reactor is designed for continuous catalytic isomerization of the n-pentane present in the second stream. The isomerization reactor is operable to maintain a partial pressure of hydrogen and operating conditions of temperature and pressure that facilitate contact between the hydrogen stream, the second stream and the isomerization catalyst to promote isomerization of the n-pentane to i-pentane while minimizing hydrocracking. The isomerization reaction is equilibrium-limited. For this reason, any n-pentane that is not converted on a first pass through the isomerization reactor may optionally be recycled to the same isomerization reactor, or converted in multiple isomerization reactors that are arranged in series configuration, thereby further increasing the ratio of i-pentane to n-pentane in the isomerization effluent. The relative efficiency of separation of pentane isomers in the first separator may be poor in embodiments that utilize distillation. Thus, separation of these isomers may be more effectively accomplished by a molecular sieve, which selectively adsorbs n-pentane due to its smaller pore diameter relative to isopentane.

In certain embodiments, the activity of the isomerization catalyst may be decreased in the presence of sulfur, thereby decreasing the isomerization rate and, consequently, the octane number of the final product. In such embodiments, the paraffins feed stream is hydrotreated to remove sulfur prior to being conveyed to the isomerization reactor.

The isomerization catalyst may comprise any known isomerization catalyst. Currently, three basic families of light naphtha isomerization catalysts are known. The first are termed super-acidic catalysts (impregnated acid type), such as, for example, chlorinated alumina catalysts with platinum. Super acidic isomerization catalysts are highly active and have significant activity at temperatures as low as 130° C. using a lower H2/HC ratio (less than 0.1 at the outlet of the reactor). However, maintaining the high acidity of these catalysts requires the addition of a few ppm of chloriding agent to the paraffins feed stream. At the inlet of the isomerization reactor, this chloriding agent reacts with hydrogen to form HCl, which inhibits the loss of chloride from the catalyst. Unlike a zeolitic catalyst, the acidic sites on a super-acidic catalyst are irreversibly deactivated by water. These catalysts are also sensitive to sulfur and oxygenate contaminants, so the paraffins feed stream is generally hydrotreated and dried to remove residual water contamination. Commercially-available examples of chlorided-alumina catalysts include, but are not limited to, IS614A, AT-2, AT-2G, AT-10 and AT-20 (by Akzo Nobel) and ATIS-2L (by Axens). Due to their chlorinated nature, these are very sensitive to feed impurities, particularly water, elemental oxygen, sulfur, and nitrogen. When using such super-acidic catalysts, the reactor operating temperature generally ranges from 14° C. to 175° C., while the operating pressure is generally in the range from 200 psig to 600 psig, preferably in the range from 425 psig to 475 psig.

Zeolitic isomerization catalysts (structural acid type) require a higher operating temperature and are effective at isomerization at temperatures ranging from 220° C. to about 315° C., preferably at a temperature ranging from 230° C. to 275° C. Pressures utilized for isomerization with zeolitic isomerization catalysts typically range from 300 psig to 550 psig with a LHSV from 0.5 to 3.0 hr$^{-1}$. These catalysts act as bifunctional catalysts and require hydrogen at a H$_2$/HC ratio ranging from about 1.5 to about 3. Zeolitic catalysts have advantages over chlorided-alumina catalysts due to zeolitic catalyst tolerance for typical catalyst poisons sulfur, oxygenates and water. Zeolitic catalysts also do not require the injection of a chloriding agent in order to maintain catalyst activity.

A third type of conventional isomerization catalyst that may be useful in certain embodiments comprises sulfated zirconia/metal oxide catalysts. These catalysts are active at relatively low temperatures (e.g., 100° C.) with the advantage of providing enhanced isoparaffin yield. Their biggest drawback is their relative sensitivity to catalyst poisons, especially water. Certainly, other examples of isomerization catalysts that are suitable for use with the present processes and systems described herein are known by those having experience in the field, and thus, require no further disclosure here.

A number of commercial processes are utilized to dehydrogenate light alkanes to produce olefins. These processes are understood by those having experience in the art and typically utilize a catalyst comprising chromium oxide on alumina (optional alkali promoter), sometimes in combination with Pt/Sn on zirconia. Alternatively, some processes utilize Pt/Sn on alumina with an alkaline promoter, or Pt/Sn on ZnAl$_2$O$_3$/CaAl$_2$O$_3$. Any other catalyst known to facilitate dehydrogenation reactions may also be utilized, including zeolites. The catalyst may optionally comprise one or more metals on a solid support, including, but not limited to Ga, Zn, Cr, Pt, Cs, Ce, Sn, Mg, Fe, Cu, W and Au.

The dehydrogenation reactor typically comprises at least one catalyst bed that may be fixed, fluidized, ebulliated or moving bed. The conditions utilized for dehydrogenation include a reaction temperature that typically ranges from 400° C. to 650° C. and a pressure that ranges from 4 psia to 75 psia. In certain embodiments, the dehydrogenation reactor may comprise more than one reactor operably connected in series configuration. In such embodiments, each of the more than one dehydrogenation reactors would contain at least one bed comprising at least one dehydrogenation catalyst.

The hydration reactor is operable to contain at least one bed of the hydration catalyst, which may comprise one or more hydration catalysts. The hydration reactor is further operable to facilitate contact between olefins, water and the hydration catalyst at a temperature that ranges from 0° C. to 150° C. and a pressure that ranges from 0 to 250 psia, thereby facilitating catalytic conversion of olefins to alcohols by the hydration catalyst Electrophilic hydration adds electrophilic hydrogen from a non-nucleophilic strong acid (a reusable catalyst, examples of which include sulfuric and phosphoric acid) and applying appropriate temperatures to break the alkene double bond. Following carbocation formation, water bonds with the carbocation to form a 1°, 2°, or 3° alcohol on the alkane. The hydration catalyst of the present inventive disclosure is typically a solid acid catalyst, such as an acid resin. One non-limiting example of such an acid is Amberlyst™ 15 resin (hydrogen form), which is a macro-reticular polystyrene based ion-exchange resin with a strongly acidic sulfonic group. It serves as an excellent source of strong acid and can be used for heterogeneous acid catalysis. Other hydration catalysts are known in the art and may be utilized (e.g., mercury) but are not preferred due to potential toxicity and cost.

The paraffins feed stream generally comprises alkanes that contain from four to nine carbon atoms. In certain embodiments the paraffins feed stream comprises at least 50 vol. % (optionally at least 60 vol. %, optionally at least 70 vol. %) alkanes that each contain from five to seven carbon atoms. In certain embodiments, the paraffins feed stream comprises at least 30 vol. % (optionally at least 40 vol. %; optionally at least 50 vol. %) pentanes. In certain embodiments, the paraffins feed stream comprises a natural gasoline (also known in the petroleum refining industry as condensate or light naphtha). Natural gasoline is an NGL product that is often produced at natural gas processing plants. Typically, natural gasoline contains about 44 to 70 vol. % of pentanes and is not a desirable gasoline blend stock due to its relatively high Reid vapor pressure (RVP) and the low average octane number of its constituent hydrocarbons. Natural gasoline predominantly comprises hydrocarbons characterized by a carbon number of five or higher (C5) and is generally characterized by a vapor pressure that lies between that of natural-gas condensate and liquefied petroleum gas (LPG). It is the only NGL which remains in a liquid state at atmospheric pressures and temperatures. Although it is volatile on its own, natural gasoline can be blended with other hydrocarbons to produce commercial motor gasoline. The molecular composition of a typical sample of natural gasoline is shown in Table 1.

TABLE 1

Composition of a typical natural gasoline sample.

| Compounds | Vol. % |
|---|---|
| butanes | 2.1 |
| iso-pentane | 35.3 |
| n-pentane | 26.7 |
| iso-hexanes | 12.0 |
| n-hexane | 7.6 |
| iso-heptanes | 3.4 |
| n-heptane | 1.4 |
| Cyclic C5, C6 | 6.2 |
| C8+ | 5.3 |
| Total: | 100.0 vol. % |
| (MON + RON)/2 | 67 |
| RVP (psia) | 14.7 |

In certain embodiments, the paraffins feed stream may alternatively comprise an FCC naphtha, which is a light fraction derived from the product effluent of a fluidized catalytic cracker.

The following examples of certain embodiments of the invention are given. Each example is intended to illustrate a specific embodiment, but the scope of the invention is not intended to be limited to the embodiments specifically disclosed. Rather, the scope is intended to be as broad as is supported by the complete disclosure and the appending claims.

Example 1

In a first example, C5 olefins were hydrated to C5 alcohols using a solid acid catalyst. A hydration reaction utilized an acid resin, Amberlyst™ 15, and was carried out in an autoclave reactor at a temperature of 65° C. and a pressure of 60 psig for 2 hrs at 1000 rpm. Fifteen grams of 2-methylbutene-2 and 6.0 grams of water were mixed and charged to an autoclave reactor. In addition, 21 grams of isopropanol was added to the mixture to improve miscibility between water and the 2-methylbutene-2.

After the reaction was completed, the hydration effluent was discharged from the reactor and analyzed for the formation of 2-methyl-2-butanol. The results indicated that 50 mass % of the C5 olefin 2-methylbutene-2 was converted to alcohols, with a specificity to 2-methyl-2-butanol of 97%. The isopropanol was separated from the product effluent for re-use.

The invention is specifically intended to be as broad as the claims below and their equivalents. It is clear that certain changes, substitutions, and alterations can be made without departing from the spirit and scope of the invention as defined by the following claims. Those skilled in the art may be able to study the preferred embodiments and identify obvious variants. It is the intent of the inventors that such obvious variants are within the scope of the claims while the description, abstract and drawings are not intended to limit the scope of the invention.

We claim:

1. A system for upgrading a paraffins feed stream to produce liquid transportation fuels, comprising:
   a. a first separator operable to receive and separate a paraffins feed stream comprising at least 50 volume percent of paraffins that contain from five to seven carbon atoms to produce a first stream that predominantly comprises paraffins containing five carbon atoms and a second stream predominantly comprising paraffins that contain six or seven carbon atoms;
   b. a dehydrogenation reactor containing at least one catalyst bed that contains at least one dehydrogenation catalyst, the dehydrogenation reactor operable to receive the first stream and to facilitate contact between the first stream and the dehydrogenation catalyst at a temperature and a pressure that facilitates catalytic olefination of paraffins in the first stream by the dehydrogenation catalyst to produce a dehydrogenation effluent that is characterized by an increased olefins content relative to the first stream;
   c. a first conduit operable to receive and combine the dehydrogenation effluent, a water stream and an isopropanol stream to produce a mixture;
   d. a hydration reactor containing at least one catalyst bed that contains at least one dehydrogenation catalyst, the hydration reactor operable to receive the mixture and to facilitate contact between the mixture and the hydration catalyst in the presence of water at a temperature and a pressure that facilitates catalytic conversion of the mixture to alcohols by the hydration catalyst to produce a hydration effluent that is characterized by an increased alcohol content (in mol. %) relative to the alcohol content of the dehydrogenation effluent;
   e. a second separator operable to receive the hydration effluent and to separate the hydration effluent to produce the isopropanol stream that predominantly comprises isopropanol and a recycle stream that predominantly comprises paraffins and olefins;
   f. a second conduit operable to receive, convey and combine the isopropanol stream with the mixture in the second conduit;
   g. a third conduit operable to receive, convey and combine the recycle stream with the first stream.

2. The system of claim 1, wherein the dehydrogenation reactor is operable to maintain a temperature in the range from 500° C. to 650° C. and a pressure in the range from 0 psia to 75 psia.

3. The system of claim 1, wherein the dehydrogenation catalyst comprises one or more metals on a solid support, wherein the one or more metals are selected from Au, Ce, Cr, Cs, Cu, Ga, Fe, Mg, Pt, Pd, Sn, W and Zn.

4. The system of claim 1, wherein the hydration reactor is operable to maintain a temperature in the range from 0° C. to 150° C. and a pressure in the range from 0 psia to 250 psia.

5. The system of claim 1, wherein the hydration catalyst comprises a solid acid catalyst.

6. The system of claim 1, further comprising a conduit that is operable to receive and convey the second stream to a blending apparatus that is operable to blend the second stream with at least one hydrocarbon stream to produce a blended fuel that meets all applicable regulatory requirements for a liquid transportation fuel.

7. A system for upgrading a paraffins feed stream to produce liquid transportation fuels, comprising:
   a. a first separator operable to receive and separate a paraffins feed stream comprising at least 50 volume percent of paraffins that contain from five to seven carbon atoms to produce a first stream predominantly comprising iso-pentane, a second stream predominantly comprising n-pentane and a third stream predominantly comprising paraffins that contain six or seven carbon atoms;
   b. a dehydrogenation reactor containing at least one catalyst bed comprising at least one dehydrogenation catalyst, the dehydrogenation reactor operable to receive the first stream and to facilitate contact between the first stream and the dehydrogenation catalyst at a temperature and a pressure that facilitates catalytic olefination of paraffins in the first stream by the dehydrogenation catalyst to produce a dehydrogenation effluent that is characterized by an increased olefins content relative to the first stream;
   c. an isomerization reactor containing at least one catalyst bed comprising at least one isomerization catalyst, the isomerization reactor operable to receive the second stream and facilitate contact between the second stream, the isomerization catalyst and a hydrogen stream at a temperature and a pressure that facilitates catalytic isomerization of n-pentane by the isomerization catalyst to produce an isomerization effluent comprising an increased content (in mol. %) of isopentane relative to the second fraction;
   d. a first conduit operable to receive, convey and combine the isomerization effluent to with the paraffins feed stream;
   e. a second conduit operable to receive and combine the dehydrogenation effluent, a water stream and an isopropanol stream to produce a mixture;
   f. a hydration reactor containing at least one catalyst bed comprising at least one hydration catalyst, the hydration reactor operable to receive the mixture and to facilitate contact between the mixture and the hydration catalyst at a temperature and a pressure that facilitates catalytic conversion of the to alcohols by the hydration catalyst to produce a hydration effluent that is characterized by an increased alcohol content (in mol. %) relative to the alcohol content of the dehydrogenation effluent;
   g. a second separator operable to receive the hydration effluent and to separate the hydration effluent to produce an isopropanol stream that predominantly comprises isopropanol and a recycle stream that predominantly comprises paraffins and olefins;

h. a third conduit operable to receive, convey and combine the isopropanol stream with the mixture in the second conduit;

i. a fourth conduit operable to receive, convey and combine the recycle stream with the first stream.

8. The system of claim 7, wherein the dehydrogenation reactor is operable to maintain a temperature in the range from 500° C. to 650° C. and a pressure in the range from 0 psia to 75 psia.

9. The system of claim 7, wherein the dehydrogenation catalyst comprises one or more metals on a solid support, wherein the one or more metals are selected from Au, Ce, Cr, Cs, Cu, Ga, Fe, Mg, Pt, Pd, Sn, W and Zn.

10. The system of claim 7, wherein the hydration reactor is operable to maintain a temperature in the range from 0° C. to 150° C. and a pressure in the range from 0 psia to 250 psia.

11. The system of claim 7, wherein the hydration catalyst comprises a solid acid catalyst.

12. The system of claim 7, wherein the isomerization reactor comprises more than one isomerization reactor arranged in series configuration, each isomerization reactor comprising at least one catalytic bed containing at least one isomerization catalyst.

13. The system of claim 7, wherein the isomerization reactor is operable to maintain a temperature in the range of 14° C. to 350° C. and a pressure in the range from 200 to 600 psig.

14. The system of claim 7, further comprising a conduit that is operable to receive and convey the third stream to a blending apparatus that is operable to blend the third stream with at least one hydrocarbon stream to produce a blended fuel that meets all applicable regulatory requirements for a liquid transportation fuel.

* * * * *